US010145853B2

United States Patent
Meno et al.

(10) Patent No.: US 10,145,853 B2
(45) Date of Patent: Dec. 4, 2018

(54) BIOMARKERS FOR NON-ALCOHOLIC FATTY LIVER DISEASE, AND METHODS FOR DETECTING NON-ALCOHOLIC FATTY LIVER DISEASE BY USING SUCH BIOMARKERS

(71) Applicant: MCBI, Inc., Tsukuba (JP)

(72) Inventors: Kohji Meno, Ushiku (JP); Hideaki Suzuki, Ryugasaki (JP)

(73) Assignee: MCBI, Inc., Tsukuba (JP)

( * ) Notice: Subject to any disclaimer, the term of this patent is extended or adjusted under 35 U.S.C. 154(b) by 0 days.

(21) Appl. No.: 14/679,332

(22) Filed: Apr. 6, 2015

(65) Prior Publication Data

US 2015/0219672 A1    Aug. 6, 2015

Related U.S. Application Data

(63) Continuation of application No. 13/119,724, filed as application No. PCT/JP2009/004657 on Sep. 16, 2009, now abandoned.

(30) Foreign Application Priority Data

Sep. 19, 2008   (JP) ................................. 2008-241863

(51) Int. Cl.
*G01N 33/68*       (2006.01)
*C07K 14/81*       (2006.01)

(52) U.S. Cl.
CPC ...... *G01N 33/6893* (2013.01); *C07K 14/8114* (2013.01); *G01N 2333/811* (2013.01); *G01N 2800/085* (2013.01)

(58) Field of Classification Search
None
See application file for complete search history.

(56) References Cited

U.S. PATENT DOCUMENTS

2011/0123501 A1* 5/2011 Chou ..................... A23K 1/009
                                                    424/93.44
2014/0273275 A1* 9/2014 Jacobs ............... G01N 33/6893
                                                    436/501

FOREIGN PATENT DOCUMENTS

JP         2006-284389 A    10/2006

OTHER PUBLICATIONS

Mayeux et al. , "Biomarkers: Potential uses and Limitations"; NeuroRx (2004); vol. 1, pp. 182-188.*
Noh et al., Inter-alpha-trypsin inhibitor heavy chain H4 as a diagnostic and prognostic indicator in patients with hepatitis B virus-associated hepatocellular carcinoma, Clinical Biochemistry, 47, (2014), p. 1257-1261.*
Mohamed et al., Lectin-based electrophoretic analysis of the expression of the 35 kDa inter-α-trypsin inhibitor heavy chain H4 fragment in sera of patients with five different malignancies, Electrophoresis, 29, (2008), p. 1-6.*
Uchida et al., English Machine Translation of JP2006-284389 (2006), (42 pages).*
Wieckowska et al., Hepatology, 46(2), (2007), p. 582-589 (Year: 2007).*
"Definition & Facts of NAFLD & NASH." https://www.niddk.nih.gov/healthy-information/liver-disease/nafld-nash/definition-facts. 2016 . Web. [Accessed Nov. 6, 2017]. (Year: 2016).*
Chandler et al., Site-specific Glycan Microheterogeneity of Inter-Alpha-Trypsin Inhibitor Heavy Chain H4, Journal of Proteome research, 13, (2014), p. 3314-3329 (Year: 2014).*
Harlow & Lane (Harlow, E. and Lane, D., Antibodies: A Laboratory Manual (1988) Cold Spring Harbor Laboratory Press, Cold Spring Harbor, NY, pp. 59-61 and 72-76 (11 pages) (Year: 1988).*
Uniprot, Q14624 (ITIH4_Human), (Entry version 69, Jan. 23, 2007) URL http://www.uniprot.org/uniprot/Q14624#.txt?version=69, Accessed on Feb. 19, 2014, 3 pages).

* cited by examiner

*Primary Examiner* — Ram R Shukla
*Assistant Examiner* — Ellen J Marcsisin
(74) *Attorney, Agent, or Firm* — Birch, Stewart, Kolasch & Birch, LLP

(57) ABSTRACT

The present invention aims to present methods to detect nonalcoholic fatty liver disease including nonalcoholic steatohepatitis by using a protein or its partial peptide that differs in presence or absence, or in quantity between healthy human subjects and patients with nonalcoholic fatty liver disease or nonalcoholic steatohepatitis or between patients with fatty liver and nonalcoholic steatohepatitis and further aims to present biomarkers comprising said protein and said partial peptide to be used to detect nonalcoholic fatty liver disease including nonalcoholic steatohepatitis. Specifically, 35 kDa protein fragment consisting of amino acid sequence expressed by Sequence No. 2 and its partial peptide consisting of amino acid sequence expressed by Sequence No. 3 (including its glycated form) of inter-alpha-trypsin inhibitor heavy chain H4 precursor consisting of amino acid sequence expressed by Sequence No. 1 could be used as biomarkers to detect nonalcoholic fatty liver disease including nonalcoholic steatohepatitis.

4 Claims, 6 Drawing Sheets

Specification includes a Sequence Listing.

BIOMARKERS FOR NON-ALCOHOLIC FATTY LIVER DISEASE, AND METHODS FOR DETECTING NON-ALCOHOLIC FATTY LIVER DISEASE BY USING SUCH BIOMARKERS

This application is a Continuation of U.S. patent application Ser. No. 13/119,724 filed on May 19, 2011, which is the National Phase of PCT International Application No. PCT/JP2009/004657 filed on Sep. 16, 2009 and claims priority to Patent Application No. 2008-241863 filed in Japan on Sep. 19, 2008, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitle "20160803_48770115PUS2_ST25.txt" created on Aug. 3, 2016 and is 12,415 bytes in size. The sequence listing contained in this .txt file is part of the specification and is hereby incorporated by reference herein in its entirety.

FIELD OF THE INVENTION

The present invention relates to novel biomarkers for nonalcoholic fatty liver disease and methods for detecting nonalcoholic fatty liver disease using such biomarkers.

BACKGROUND OF THE INVENTION

The commonly used means to differentiate between normal and non-normal states of a human subject using his or her biological materials are mainly those which have been used in the field of diagnostics. Most frequently used are those methods which target biomarkers in blood. It has been practiced in this field to comparatively measure the amount of a specific protein or a peptide that is less than 10,000 in molecular weight or, in the case of enzyme protein, enzyme activities in samples from normal (healthy) subjects and those from diseased individuals to help diagnosis. Here, prior to testing real samples, measurements are done on a fixed number each of samples from healthy controls and patients with certain disease with respect to the amount(s) or activity (activities) of single or multiple specific proteins or peptides and the ranges of abnormal and normal values are respectively determined. The sample to be evaluated is then analyzed by the same method and the resultant value is judged with respect to whether it is in normal or abnormal range.

In the actual measurements, the amount(s) of specified protein(s) or peptide(s) in test samples, as such or after dilution, are determined by the use of enzyme-linked immmunosorbent assay (ELISA) which uses a primary, or secondary, antibody labeled with an enzyme reacting with a substrate that yields a color upon reaction, chemiluminescent immunoassay (CLIA), radioimmunoassay (RIA) which uses a primary, or secondary, antibody labeled with a radioisotope, and, if the protein is an enzyme, the measurement of the activity of the enzyme by adding its substrate and determining the intensity of produced color, etc. These antibody-based methods are called as enzyme-, fluorescence- or radioisotope-labeled methods, respectively. In addition, there is a method where an enzyme reaction product derived from the corresponding substrate is determined by high performance liquid chromatography (HPLC). In further addition, there is a method where HPLC is combined with mass spectrometer, called LC-MS/MS, and there is a method called selected reaction monitoring (SRM)/multiple reaction monitoring (MRM) that utilizes LC-MS/MS. In another method to determine the concentration in a sample, it is appropriately pretreated, and separation of proteins or peptides is attained by 2-dimensional polyacrylamide gel electrophoresis (2D-PAGE), and target protein or peptide is determined by silver staining, Coomassie blue staining or immunological staining (Western blotting) that uses an antibody to target protein or peptide. In still further addition, there is a method which utilizes mass spectrometry to determine the amount of target protein or peptide in samples fractionated by column chromatography. Instead of column chromatography, protein chips and magnetic beads may also be utilized for purpose of pretreatment.

Furthermore, these inventors have developed an immunoMS method, where target protein or peptide is captured by beads (including magnetic ones) with linked antibody to the protein or peptide, eluted from the beads, and determined by mass spectrometry. Further, intact proteins have been reported to be analyzed by mass spectrometry using abovementioned methods after digestion with trypsin etc. (Patent Document 1). Here, intact target proteins are selected either by fractionation or by adsorption to an adsorbant specific to them and then determined by mass spectrometry.

Nonalcoholic fatty liver disease is abbreviated as NAFLD and patients with this disease, despite the fact that they have no drinking habit (less than 20 g daily), give histological findings characterized by hepatic fatty deposition reminiscent of those found in alcoholic hepatic damage. The disease caused viruses such as HCV or HBV or of autoimmune origin is excluded. The disease is regarded as a phenotype in the liver of metabolic syndrome accompanying obesity. NAFLD is divided into simple fatty liver and nonalcoholic steatohepatitis. The latter, abbreviated as NASH, is a progressive disease. NASH frequently accompanies fibrosis and has been known to often progress to hepatic cirrhosis and further to hepatic cancer. These features have attracted attention to this disease (Non-patent Document 1). Hereafter in this specification, simple fatty liver is called fatty liver.

Fatty liver is suspected in regular checkups from high levels of triglyceride in blood and diagnosed by abdominal ultrasonography and CT. Attention is warranted to the fact that 40% of fatty liver in non-drinker is accompanied by hepatic damage. Despite the observation that nonalcoholic fatty liver progresses to NASH, no convenient blood test is available for NASH.

While NASH is regarded as a severe type of NAFLD, routine blood chemistry, specifically the values of alanine aminotransferase (ALT) and aspartate aminotransferase (AST) increase only slightly and the disease is often overlooked. Hence, it has been pointed out to be an important issue requiring resolution because there is no specific test method to detect it as in the case of fatty liver.

CITATION LIST

Patent Document

Patent Document 1, JP-A-2004-333274
Patent Document 2, JP-A-2006-308533

Non-Patent Document

Non-Patent Document 1, "A Guide to Diagnosis and Treatment of NASH and NAFLD," edited by Japanese Hepatology Association, 2006 (in Japanese)
Non-Patent Document 2, Benkirane, N. et al, J. Biol. Chem. Vol. 268, 26279-26285, 1993

SUMMARY OF INVENTION

Problems to be Solved by the Invention

The present invention aims to present methods to detect nonalcoholic fatty liver disease including nonalcoholic steatohepatitis by using a protein or its partial peptide that differs in presence or absence, or in quantity between healthy human subjects and patients with nonalcoholic fatty liver disease or nonalcoholic steatohepatitis and further aims to present biomarkers comprising said protein and said partial peptide to be used to detect nonalcoholic fatty liver disease including nonalcoholic steatohepatitis.

Solution to Problem

These inventors investigated to find out means to detect nonalcoholic fatty liver disease and found a protein fragment and its partial peptide capable of detecting nonalcoholic fatty liver disease including nonalcoholic steatohepatitis among liver disease biomarkers which these inventors had found previously.

Specifically, these inventors found that a 35 kDa protein fragment consisting of amino acid sequence expressed by SEQ ID NO:2 and its partial peptide consisting of amino acid sequence expressed by SEQ ID NO:3 (including its glycated form) of inter-alpha-trypsin inhibitor heavy chain H4 precursor consisting of amino acid sequence expressed by SEQ ID NO:1 could be used as biomarkers to detect nonalcoholic fatty liver disease including nonalcoholic steatohepatitis.

These inventors brought the present invention to perfection by further succeeding in determining this protein fragment and its partial peptide by using immunoblot procedure and immunoMS method and confirming the enabling construction of ELISA.

The features of the invention are shown below.

[1] A biomarker for detection of nonalcoholic fatty liver disease comprising at least one protein or peptide selected from the group consisting of inter-alpha-trypsin inhibitor heavy chain H4 precursor consisting of amino acid sequence expressed by SEQ ID NO:1, 35 kDa protein fragment consisting of amino acid sequence expressed by SEQ ID NO:2 of inter-alpha-trypsin inhibitor heavy chain H4 precursor, and partial peptide consisting of amino acid sequence expressed by SEQ ID NO:3 of inter-alpha-trypsin inhibitor heavy chain H4 precursor.

[2] A biomarker for detection of nonalcoholic fatty liver disease comprising protein fragment or peptide of not less than 5 amino acid residues arising from at least one protein or peptide selected from the group consisting of inter-alpha-trypsin inhibitor heavy chain H4 precursor consisting of amino acid sequence expressed by SEQ ID NO:1, 35 kDa protein fragment consisting of amino acid sequence expressed by SEQ ID NO:2 of inter-alpha-trypsin inhibitor heavy chain H4 precursor, and partial peptide consisting of amino acid sequence expressed by SEQ ID NO:3 of inter-alpha-trypsin inhibitor heavy chain H4 precursor.

[3] A biomarker for detection of nonalcoholic steatohepatitis comprising at least one protein or peptide selected from the group consisting of inter-alpha-trypsin inhibitor heavy chain H4 precursor consisting of amino acid sequence expressed by SEQ ID NO:1, 35 kDa protein fragment consisting of amino acid sequence expressed by SEQ ID NO:2 of inter-alpha-trypsin inhibitor heavy chain H4 precursor, and partial peptide consisting of amino acid sequence expressed by SEQ ID NO:3 of inter-alpha-trypsin inhibitor heavy chain H4 precursor.

[4] A biomarker for detection of nonalcoholic steatohepatitis comprising protein fragment or peptide of not less than 5 amino acid residues arising from at least one protein or peptide selected from the group consisting of inter-alpha-trypsin inhibitor heavy chain H4 precursor consisting of amino acid sequence expressed by SEQ ID NO:1, 35 kDa protein fragment consisting of amino acid sequence expressed by SEQ ID NO:2 of inter-alpha-trypsin inhibitor heavy chain H4 precursor, and partial peptide consisting of amino acid sequence expressed by SEQ ID NO:3 of inter-alpha-trypsin inhibitor heavy chain H4 precursor.

[5] Method for detection of nonalcoholic fatty liver disease involving determination in biological material of at least one biomarker for nonalcoholic fatty liver disease described either in [1] or [2].

[6] Method for detection of nonalcoholic steatohepatitis involving determination in biological material of at least one biomarker for nonalcoholic fatty liver disease described either in [3] or [4].

[7] Method for detection of nonalcoholic fatty liver disease in which patient is judged as suffering from nonalcoholic fatty liver disease when, after determination in biological material of at least one biomarker for nonalcoholic fatty liver disease described either in [1] or [2], said biomarker is found to be present in higher quantity than in normal controls.

[8] Method for detection of nonalcoholic steatohepatitis in which patient is judged as suffering from nonalcoholic steatohepatitis when, after determination in biological material of at least one biomarker for nonalcoholic steatohepatitis described either in [3] or [4], said biomarker is found to be present in higher quantity than in normal controls.

[9] Method for detection of nonalcoholic fatty liver disease described either in [5] or [7] wherein detection is made either by immunoblot procedure, Western blotting, enzyme-, fluorescence-, or radioisotope-labeled antibody method, mass spectrometry, immunoMS method or surface plasmon resonance method.

[10] Method for detection of nonalcoholic steatohepatitis described either in [6] or [8] wherein detection is made either by immunoblot procedure, Western blotting, enzyme-, fluorescence-, or radioisotope-labeled antibody method, mass spectrometry, immunoMS method or surface plasmon resonance method.

[11] A kit for detection of nonalcoholic fatty liver disease to determine at least one biomarker described either in [1] or [2].

[12] A kit for detection of nonalcoholic steatohepatitis to determine at least one biomarker described either in [3] or [4].

[13] A kit for detection of nonalcoholic fatty liver disease containing antibody or aptamer to at least one biomarker described either in [1] or [2].

[14] A kit for detection of nonalcoholic steatohepatitis containing antibody or aptamer to at least one biomarker described either in [3] or [4].

[15] A kit for detection described either in [13] or [14] wherein antibody or aptamer is solidified on a plate or plates.

Advantageous Effect of the Invention

According to the present invention, it is possible to diagnose a subject as to whether said subject has suffered from nonalcoholic fatty liver disease or nonalcoholic steatohepatitis by determining in biological material obtained from said subject the kind and amount of at least one protein or at least one partial peptide derived by digestion, etc. of said protein selected from the group consisting of inter-alpha-trypsin inhibitor heavy chain H4 precursor consisting of amino acid sequence expressed by SEQ ID NO:1, 35 kDa protein fragment consisting of amino acid sequence expressed by SEQ ID NO:2 of inter-alpha-trypsin inhibitor heavy chain H4 precursor, and partial peptide consisting of amino acid sequence expressed by SEQ ID NO:3 of inter-alpha-trypsin inhibitor heavy chain H4 precursor.

The present invention presents a diagnostic system that is high in both accuracy and specificity. The present invention enables highly accurate diagnosis of nonalcoholic fatty liver disease and nonalcoholic steatohepatitis in which there have been no specific test methods for such biological materials as blood. It is also possible with the present invention to diagnose the degree to which the liver disease has progressed to hepatic cancer. Further, the biomarkers disclosed in the present invention are highly useful in judgment of drug efficacy.

DESCRIPTION OF EMBODIMENTS

Figure 1:
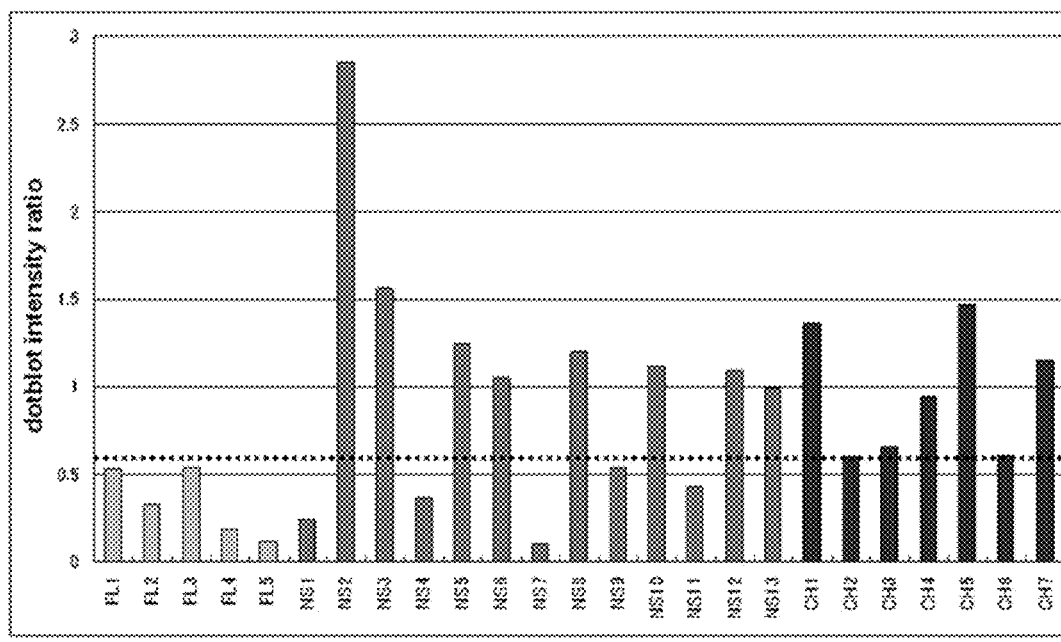
FIG. 1 illustrates the results of applying immunoblot method using BMPEP1117R as primary antibody in patients with fatty liver (FL), nonalcoholic steatohepatitis (NS) and chronic hepatitis (CH).

The present invention is a method for determining the kind and the amount of intact protein and/or its partial peptide when test subject is suffering from nonalcoholic fatty liver disease or nonalcoholic steatohepatitis as well as for diagnosing whether test subject is suffering from non-alcoholic fatty liver disease or nonalcoholic steatohepatitis and, if test subject is diagnosed to be suffering from nonalcoholic fatty liver disease or nonalcoholic steatohepatitis, for elucidating the degree to which the liver disease has progressed. A peptide is generally said to be a chemical entity, made by polymerizing a number of amino acids, of less than 10,000 in molecular weight or by polymerizing several to less than about 50 amino acid residues. While in the present invention a partial peptide of an intact protein can be used as a biomarker for detection of nonalcoholic fatty liver disease or nonalcoholic steatohepatitis, such partial peptide is defined as a peptide of less than 10,000 in molecular weight consisting of a part of the amino acid sequence of the intact protein. Such peptide may arise as a partial peptide during the expression by transcription followed by synthesis by translation before maturing into an intact protein or as a peptide produced by enzyme digestion in the body after the intact protein has been synthesized. It is possible that, when the body is in abnormal state suffering from such disease as nonalcoholic fatty liver disease or nonalcoholic steatohepatitis, the mechanism for protein synthesis and regulation is de-regulated. In other words, the present invention is also a method for determining if test subject is in normal state or is suffering from either nonalcoholic fatty liver disease or nonalcoholic steatohepatitis by using the degree of protein synthesis and/or protein digestion as an indicator. The detection of nonalcoholic fatty liver disease or nonalcoholic steatohepatitis in the present invention means evaluation and differentiation, i.e., diagnosis of test subject as to whether the subject is suffering from nonalcoholic fatty liver disease or nonalcoholic steatohepatitis. The present invention can also include the evaluation of patient's risk of suffering from more serious liver disease.

Specifically, in the method of the present invention, the examples of intact protein that can be used as a biomarker for nonalcoholic fatty liver disease or nonalcoholic steatohepatitis include inter-alpha-trypsin inhibitor heavy chain H4 precursor consisting of amino acid sequence expressed by SEQ ID NO:1 and the 35 kDa protein fragment consisting of amino acid sequence expressed by SEQ ID NO:2. Further biomarkers for nonalcoholic fatty liver disease or nonalcoholic steatohepatitis of the present invention include any protein fragment of greater than 10,000 in molecular weight arising from inter-alpha-trypsin inhibitor heavy chain H4 precursor consisting of amino acid sequence expressed by SEQ ID NO:1 and the 35 kDa protein fragment consisting of amino acid sequence expressed by SEQ ID NO:2.

Still further, an example of biomarkers for nonalcoholic fatty liver disease or nonalcoholic steatohepatitis of the present invention includes the partial peptide consisting of amino acid sequence expressed by SEQ ID NO:3 of inter-alpha-trypsin inhibitor heavy chain H4 precursor. In the present invention, proteins and peptides consisting of amino acid sequences derived from SEQ ID NOs:1 through 3 by deletion, exchange, and/or addition of one or a few amino acids can be used as biomarkers and are included in the present invention. "One or a few" herein means "one or three," "one or two," or "one." Furthermore, the partial peptides that can be used as biomarkers in the present invention include those peptide fragments consisting of not less than 5 amino acid residues arising respectively from inter-alpha-trypsin inhibitor heavy chain H4 precursor consisting of amino acid sequence expressed by SEQ ID NO:1, the 35 kDa protein fragment consisting of amino acid sequence expressed by SEQ ID NO:2 of inter-alpha-trypsin inhibitor heavy chain H4 precursor, and the partial peptide consisting of amino acid sequence expressed by SEQ ID NO:3 of inter-alpha-trypsin inhibitor heavy chain H4 precursor. The basis for the limitation of peptide fragments consisting of not less than 5 amino acid residues is in the description below in Non-patent Document 2. The document reported that an antibody obtained by using the peptide IRGERA (SEQ ID NO: 4) as immunogen, which was the C-terminus (130-135) of histone H3, recognized the peptide IKGERA (SEQ ID NO: 5) derived by exchange of K for R and the peptide CGGGERA (SEQ ID NO: 6) which was derived by deletion of IR followed by addition of CGG. This demonstrates that the immunogenicity (antigenicity) is recognized by a peptide of not less than 4 amino acid residues. In order to expand this finding to other peptides than the C-terminus of histone H3, the number of amino acid residue is defined as not less than 5 instead of 4 in the present invention. To make such a low molecular weight peptide as the subject of the present invention is important when the method of detection and differentiation uses immunological means including immunoblot, ELISA and immunoMS.

It is to be noted that there are cases where a sugar chain or sugar chains have been added to an intact protein or its partial peptide to form glycated entities. Proteins and partial peptides in glycated form can also be used as biomarkers for detection of nonalcoholic fatty liver disease or nonalcoholic steatohepatitis. An example of such glycated peptides is the peptide of SEQ ID NO:3.

It is also to be noted that, in the present invention, biomarker can be quantified or its presence or absence can be determined qualitatively.

Two-dimensional electrophoresis (2-DE) or 2-dimensional chromatography (2-DC) can be used in the present invention to separate biomarkers in biological materials including serum. Known chromatographic methods can be selected from ion-exchange chromatography, reverse-phase chromatography and gel-filtration chromatography. It is also possible to make quantification with the SRM/MRM method in LC-MS/MS technology. Furthermore, the immunoMS method which these inventors have developed, where target protein or peptide is captured by beads (including magnetic ones) with antibody linked to the protein or peptide, eluted from the beads, and determined by mass spectrometry enables convenient determination of presence or absence or the amount of target protein, protein fragment or peptide without the use of 2-DE or chromatography.

It is possible with the use of the method disclosed in the present invention to evaluate the prognostic risk of nonalcoholic fatty liver disease in test subject and therefore it can be useful in prophylactic medicine. Further, when diet therapy and/or drug therapy is given to patients with nonalcoholic fatty liver disease, the disease progresses toward the direction of healing and, consequently, the types and the amounts of proteins and partial peptides change.

The kind and amount of a protein in biological materials can be determined by various methods. If target protein (including protein fragment and partial peptide) has been characterized and when an antibody (primary antibody) to it has already been obtained, the following methods can be used:

1. Immunoblot

This is one of the simplest methods. Test serum in a fixed amount (about 1 microliter) after stepwise dilution is dropped onto an appropriate membrane such as of nitrocellulose and dried in air. The membrane is treated with a blocking solution containing a protein such as BSA, washed, reacted with primary antibody, and washed. Thereafter, the membrane is reacted with labeled secondary antibody to detect the primary antibody. The membrane is washed and the label is visualized to measure its density.

2. Western Blotting

After separation with one-dimensional or two-dimensional electrophoresis involving isoelectric focusing or SDS-PAGE, proteins are transferred onto such an appropriate membrane as of nitrocellulose and their amounts are determined, as in above-mentioned immunoblot, using primary antibody and labeled secondary antibody.

3. ELISA

Antibody to protein or its partial peptide is fixed to such a plate as a chemically modified microtiter plate. Appropriate amounts of samples after stepwise dilution are applied to the plate and incubated. Proteins and peptides not captured are removed by washing. Next, the plate is incubated with secondary antibody labeled with fluorescent or chemiluminescent substance or enzyme. After addition of respective substrate, fluorescence, chemiluminescence or visible light due to enzyme reaction is measured for evaluation and judgment.

Additional examples of methods are illustrated below (see Patent Document 2) but the invention is not limited by these examples.

4. Methods that Use Microarray (Microchip)

A microarray is a general term for devices where solidified materials with affinity for target substances are arrayed on solid support (plate). In the present invention, antibodies or a tamers to proteins and partial peptides are arrayed. A sample of biological material is placed on the microarray for fixation of target proteins or partial peptides and the microarray is then incubated with secondary antibody labeled with fluorescent or chemiluminescent substance or enzyme. After addition of respective substrate, fluorescence, chemiluminescence or visible light due to enzyme reaction is measured.

5. Mass Spectrometry

In mass spectrometry, for example, antibody to a specified protein or partial peptide is attached to chemically modified microbeads or plate (protein chip). The microbeads could be magnetic beads. There are no requirements for the material of the plate. The antibody to be used could be (1) an antibody which recognizes the full length form of the specified protein only, (2) an antibody which recognizes a partial peptide only, (3) all of antibodies which recognizes both the specified protein and its partial peptide, or a combination of (1) and (2), (1) and (3), or (2) and (3). Samples after stepwise dilution with original solvent or buffer are added to the microbeads or plate carrying antibody or antibodies and incubated. Those proteins and partial peptides not captured are removed by washing. The protein or partial peptide captured by microbeads or plate is eluted, and analyzed by mass spectrometry with MALDI-TOF-MS, SELDI-TOF-MS, etc. Measurements are made with respect to the mass and intensity of the peak due to the protein, protein fragment or partial peptide. Prior to the measurements a fixed amount of substance serving as the internal standard is added to the original biological material and the intensity of its peak is also measured. The concentration of the target in the original biological material can be calculated from the ratio of peak intensity of the target to the peak intensity of the internal standard. This is called immunoMS method. Further, it is possible to make quantification, after the sample is diluted with original solvent or buffer, or after part of proteins are removed, by separation with HPLC followed by mass spectrometry with electrospray ionization (ESI) method. Therein the SRM/MRM method can be utilized for absolute quantification with the use of an isotope-labeled internal standard peptide.

Furthermore, in addition to the above-mentioned methods, it is possible to analyze proteins and partial peptides by using 2-DE, surface plasmon resonance, etc.

The present invention includes the method to detect nonalcoholic fatty liver disease or nonalcoholic steatohepatitis from the presence or absence of the above-mentioned biomarker after applying biological material obtained from test subject to 2-DE or surface plasmon resonance.

EXAMPLES

The present invention is further illustrated by, though in no way limited to, the following examples.

Example 1

Preparation of antibody (BMPEP1117R) specific to the N-terminus of SEQ ID NO:2

Rabbits were immunized with RLAILPASC (SEQ ID NO:7) conjugated to keyhole limpet hemocyanin (KLH)

and, after a certain period of time, blood was collected, and the antibody was obtained from it by purification by adsorption to a column to which the corresponding peptide had been attached. SEQ ID NO:2 is part of SEQ ID NO:1. SEQ ID NO:3 is located at the N-terminus of SEQ ID NO:2 and the peptide consisting of SEQ ID NO:3 is detected in the sera of patients with liver disease.

```
SEQ ID NO:1: Inter-alpha-trypsin inhibition heavy chain
H4 precursor
  001  MKPPRPVRTC SKVLVLLSLL AIHQTTTAEK NGIDIYSLTV DSRVSSRFAH

051  TVVTSRVVNR ANTVQEATFQ MELPKKAFIT NFSMNIDGMT YPGIIKEKAE

101  AQAQYSAAVA KGKSAGLVKA TGRNMEQFQV SVSVAPNAKI TFELVYEELL

151  KRRLGVYELL LKVRPQQLVK HLQMDIHIFE PQGISFLETE STFMTNQLVD

201  ALTTWQNKTK AHIRFKPTLS QQQKSPEQQE TVLDGNLIIR YDVDRAISGG

251  SIQIENGYFV HYFAPEGLTT MPKNVVFVID KSGSMSGRKI QQTREALIKI

301  LDDLSPRDQF NLIVFSTEAT QWRPSLVPAS AENVNKARSF AAGIQALGGT

351  NINDAMLMAV QLLDSSNQEE RLPEGSVSLI ILLTDGDPTV GETNPRSIQN

401  NVREAVSGRY SLFCLGFGFD VSYAFLEKLA LDNGGLARRI HEDSDSALQL

451  QDFYQEVANP LLTAVTFEYP SNAVEEVTQN NFRLLFKGSE MVVAGKLQDR

501  GPDVLTATVS GKLPTQNITF QTESSVAEQE AEFQSPKYIF HNFMERLWAY

551  LTIQQLLEQT VSASDADQQA LRNQALNLSL AYSFVTPLTS MVVTKPDDQE

601  QSQVAEKPME GESRNRNVHS GSTFFKYYLQ GAKIPKPEAS FSPRRGWNRQ

651  AGAAGSRMNF RPGVLSSRLL GLPGPPDVPD HAAYHPFRRL AILPASAPPA

701  TSNPDPAVSR VMNIKIEETT MTTQTPAPIQ APSAILPLPG QSVERLCVDP

751  RHRQGPVNLL SDPEQGVEVT GQYEREKAGF SWIEVTFKNP LVWVHASPEH

801  VVVTRNRRSS AYKWKETLFS VMPGLKMTMD KTGLLLLSDP DKVTIGLLFW

851  DGRGEGLRLL LRDTDRFSSH VGGTLGQFYQ EVLWGSPAAS DDGRRTLRVQ

901  GNDHSATRER RLDYQEGPPG VEISCWSVEL

SEQ ID NO:2: 35 kDa protein fragment of inter-alpha-trypsin
inhibitor heavy chain H4 precursor
  001  RLAILPASAP PATSNPDPAV SRVMNIKIEE TTMTTQTPAP IQAPSAILPL

051  PGQSVERLCV DPRHRQGPVN LLSDPEQGVE VTGQYEREKA GFSWIEVTFK

101  NPLVWVHASP EHVVVTRNRR SSAYKWKETL FSVMPGLKMT MDKTGLLLLS

151  DPDKVTIGLL FWDGRGEGLR LLLRDTDRFS SHVGGTLGQF YQEVLWGSPA

201  ASDDGRRTLR VQGNDHSATR ERRLDYQEGP PGVEISCWSV EL
```

SEQ ID NO:3: Partial peptide of inter-alpha-trypsin inhibitor heavy chain H4 precursor
RLAILPASAPPATSNPD The above-described peptide was present in serum in the glycated state shown below. RLAILPASAPPATSNPD to which -GlcNAc-Hex-GlcNAc-Hex has been added.

Example 2

Application of immunoblot method using BMPEP1117R as the primary antibody to sera from healthy controls and patients with fatty liver, nonalcoholic steatohepatitis, and chronic hepatitis The following materials were used. Membrane, 0.22 μm MF-millipore membrane filter; TBS, 20 mM Tris-HCl containing 0.15 M NaCl (pH 7.5); TBSt, TBS containing 0.05% Tween 20; blocking solution, TBSt containing 5% BSA; BSA-TBSt, TBSt containing 0.1% BSA.

The procedures were as follows. Grids of 5 mm size each were drawn on the membrane. One 1 μL of serum sample prediluted with TBS was dropped onto each grid, the membrane was air-dried and immersed in the blocking solution. The membrane was washed with TBSt, and to it 2 mL of the primary antibody (BMPEP1117R, 0.68 μg/mL) in BSA-TBSt was added and it was left standing. The membrane was then washed with TBSt and to it 2 mL of the secondary antibody (HRP conjugated anti-rabbit IgG, 1:5000, GE Healthcare) in BSA-TBSt was added and it was left standing. The membrane was washed several times with TBSt and further washed with TBS. The chemiluminescence intensity of each spot is measured. Serum samples from a patient with chronic hepatitis after stepwise dilution with TBS were placed on each membrane and served as control.

The sample from each subject or patient was tested in duplicate. The ratio in chemiluminescence intensity of 125-fold diluted sample to 125-fold diluted control on the same membrane, called herein "dotblot intensity ratio," was determined and the mean of the duplicate determinations was calculated.

FIG. 1 is a bar graph showing the above-mentioned mean values of dotblot intensity ratio. FL means patients with fatty liver, NS those with NASH, and CH those with chronic hepatitis. The stippled line indicates the intensity ratio of 0.6 as a threshold value. The cases exceeding this threshold value were 0/5 in FL, 8/13 in NASH, and 7/7 in CH. Increased values were seen in high frequency in NASH. As will be shown in Example 3, the intensity observed in the immunoblot reflects the serum concentration of the 35 kDa protein fragment of inter-alpha-trypsin inhibitor heavy chain H4 precursor. Said 35 kDa protein fragment therefore was demonstrated to be useful in detection of not only chronic hepatitis but of fatty liver disease, particularly NASH.

Example 3

Confirmation of the fact that the immunoblot in Example 2 really determined the 35 kDa protein fragment of inter-alpha-trypsin inhibitor heavy chain H4 precursor Before analysis, serum samples were treated with Agilent Multiple Affinity Removal System (column size, 4.6 mm×100 mm) to remove albumin, IgG, IgA, transferrin, heptoglobin, and antitrypsin. Thus, serum (35 µL) was mixed with 175 µL Buffer A, insoluble materials were eliminated by using 0.45 µm centrifuge filter and 200 µL of it was applied to the system. Thereafter Buffer A was loaded at 0.5 µL/min for 10 min. The flow-through was concentrated with Microcon 10 (MILLIPORE) and, after addition of 20 mM phosphate buffer (pH 7.0), further concentrated to the final volume of less than 50 µL. After the protein content of the concentrate was determined, 150 µg of it was subjected to SDS-PAGE (10% acryl amide gel) followed by Western blotting. Thus, the SDS-PAGE gel was transferred to PVDF membrane, blocking was carried out with 5% skim milk in TBSt overnight, and the membrane was washed with TBSt and reacted thereafter with the primary antibody (BMPEP1117R, 0.68 µg/mL) for 1 h followed by washing with TBSt. Next, the membrane was reacted with the secondary antibody (HRP conjugated anti-rabbit IgG, 1:5000, GE Healthcare) and washed with TBSt. Detection was carried out using LAS3000 (Fuji Film).

Figure 2:
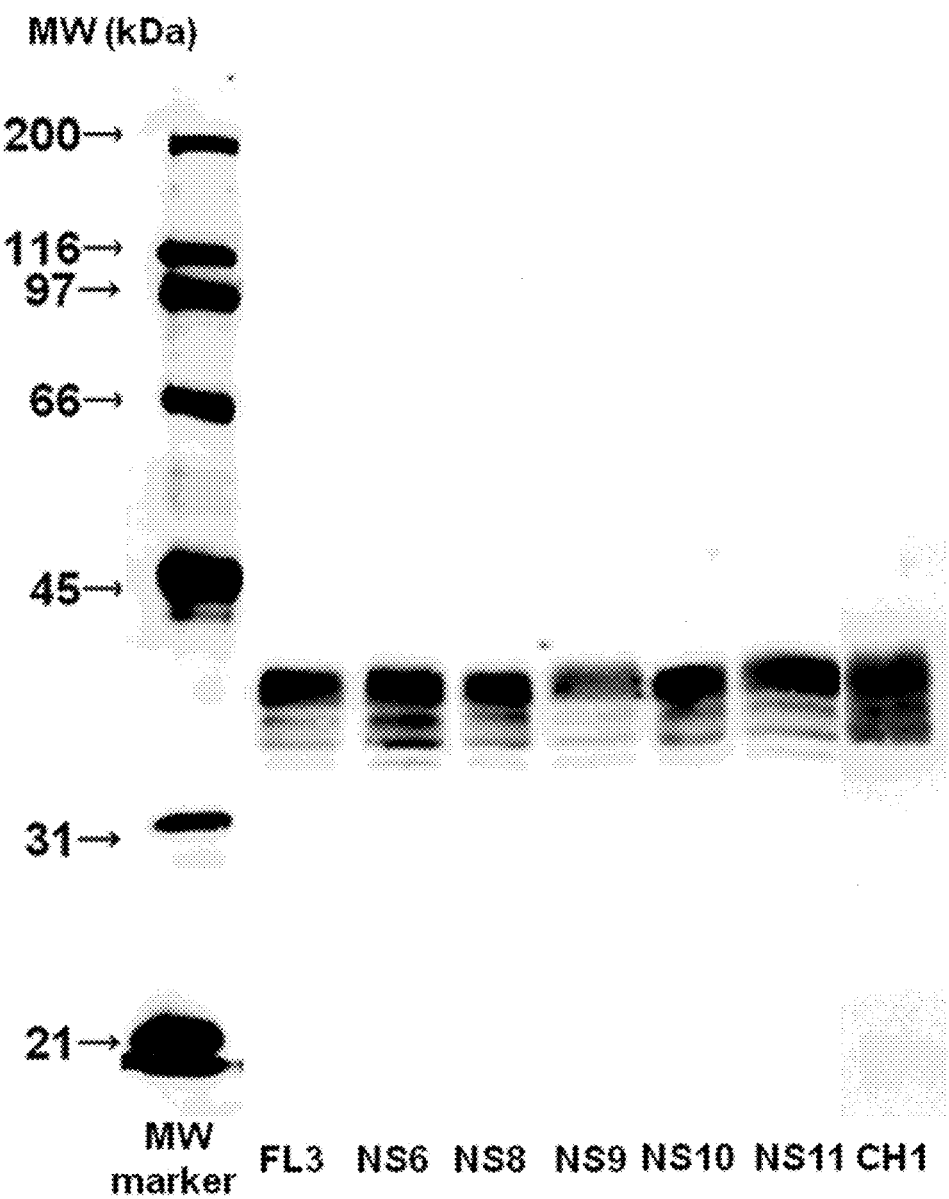
FIG. 2 proves that the immunoblot shown in FIG. 1 of Example 2 determined the 35 kDa protein fragment of inter-alpha-trypsin inhibitor heavy chain H4 precursor.

FIG. 2 illustrates the results of the above testing. The sample IDs for FL, NS, CH are identical to those shown in Example 2. A comparison with MW markers reveals that the bands are located at approximately 35 kDa. FIG. 2 also indicates that there is no band that reacts with the primary antibody (BMPEP1117R) other than the bands at approximately 35 kDa. This further indicates that each of the immunoblot data obtained in Example 2 equals the sum of the intensities resulting from these bands only. In other words, the intensity observed in the immunoblot experiment reflects the total serum concentration of the 35 kDa protein fragment of inter-alpha-trypsin inhibitor heavy chain H4 precursor. The presence of 3 or 4 bands is explained by the diversity of sugar chains attached to the protein as the 35 kDa protein fragment of inter-alpha-trypsin inhibitor heavy chain H4 precursor is known to be present in isoforms differing in the degree of glycation with acidic sugars. This is supported by the fact that, as shown in Example 5, the use of an antibody specific to the C-terminus of the 35 kDa protein fragment of inter-alpha-trypsin inhibitor heavy chain H4 precursor also reveals multiple bands similar to those seen in FIG. 2.

Example 4

Determination of serum concentration by immunoMS method of partial peptide in glycated state (see under SEQ ID NO:3) consisting of amino acid sequence expressed by SEQ ID NO:3 of inter-alpha-trypsin inhibitor heavy chain H4 precursor Beads to be used for the immunoMS method were prepared as follows:

The magnetic beads, Magnosphere MS300/Carboxyl type (JSR Co. Ltd., Tokyo), were supplied in slurry (10 mg beads/mL). MES was used as 0.1 M MES (pH 5.0, pH adjusted with NaOH).

EDC means 1-ethyl-3-(3-dimethylaminopropyl) carbodiimide hydrochloride and was prepared just before use in the concentration of 10 mg/mL (52.2 mM) in ice-cold MES. One milliliter of dispersed beads slurry (10 mg beads) was transferred into a 2.0 ml-capacity microtube. The magnetic beads were separated from supernatant by precipitation on a magnetic stand and washed with 1.0 mL MES. A solution of antibody, BMPEP1117R, was added to the magnetic beads and stirred slowly at room temperature. EDC (100 µL) was added and stirred slowly to allow reaction to take place. Washing with TBSt was repeated 4 times and beads in 1 mL TBSt were stored at 4° C.

The measurement using the immunoMS method began with addition of a fixed amount of pure peptide labeled with stable isotope as the internal standard to each serum sample. Two microliter of stable isotope-labeled peptide solution (100 fmol/µL) dissolved in 0.1% TFA-50% acetonitrile was added to 25 µL serum. This was called "A." The stable isotope-labeled peptide was obtained by exchanging 12C and 14N of the 6th P of RLAILPASAPPATSNPD (SEQ ID NO.: 8) respectively with 13C and 15N. The mean m/z $[M+H]^+$ for the unlabeled peptide was 1691.93 while that for the labeled peptide was 1697.89. It was the purpose of this testing to measure the glycated peptide of mean m/z $[M+H]^+$ 2422 in serum. While it was possible to use non-glycated form of the peptide RLAILPASAPPATSNPD (SEQ ID NO: 8) for standardization as its serum concentrations were observed to be very low, the stable isotope-labeled peptide was used for standardization in case the serum concentration of the non-glycated peptide might actually vary significantly.

The next step was pretreatment of serum sample. "A" described above was mixed with 475 µL 0.1% TFA and heated at 100° C. for 15 min. The mixture was cooled in ice, sonicated, and centrifuged. The resulting supernatant was transferred to microcon 10 (MILLIPORE) and centrifuged at 14000×g, 4° C. for 80 min. The filtrate was mixed with 500 pt 100 mM Tris-HCl (pH 7.5) containing 0.3 M NaCl and 0.2% octylglucoside and the resultant mixture was used as sample solution for the next step.

The procedures for immunoprecipitation with the magnetic beads and preparation of samples for mass spectrometry were as follows:

The magnetic beads suspension (20 µL) was added to the sample solution above and the mixture was stirred slowly. Washing and removal of the supernatant was carried out using the magnetic stand. Washing was repeated several times with TBS and finally with 50 mM ammonium bicarbonate (pH 7.5). Target peptide was eluted from the beads with 50 µL 2-propanol:H$_2$O:formic acid (4:4:1) solution twice. The recovered eluate (approximately 100 µL) was dried by a vacuum pump. The dried sample was redissolved in 20 µL 0.095% TFA-5% acetonitrile under sonication (160 W), and applied to C18 tip (PerfectPure C18 Tip, Eppendolf) for adsorption, and the tip was washed with 0.1% TFA. Peptides were eluted with 2 µL 0.1% TFA-50% acetonitrile, transferred onto the target plate for mass spectrometry, and dried. Next, 1 µL of matrix solution, i.e., 0.3 mg/mL CHCA in ethanol:acetone (2:1) was dropped onto the dried sample, and the target plate was again dried.

A MALDI-TOF-MS instrument, AXIMA CFR, was used for mass spectrometry. Measurements were done in linear mode. As 200 fmol of the internal standard was contained in each serum sample, the number of fmols in sample could be calculated by multiplying the intensity ratio of sample to internal standard times 200.

Figure 3:
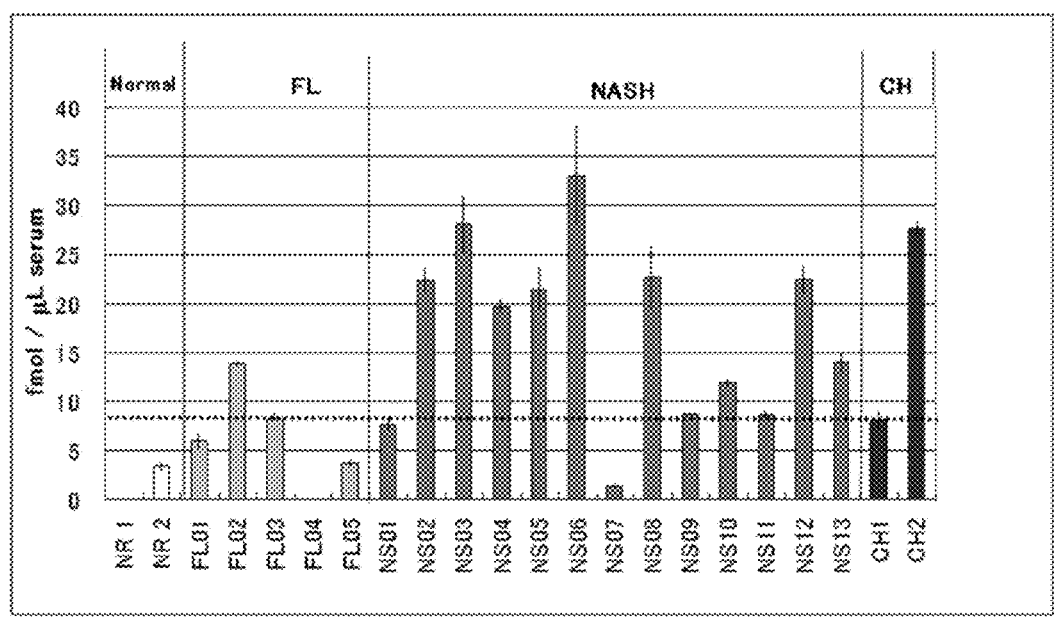
FIG. 3 illustrates the results of determination by immunoMS method of serum concentration of glycated partial peptide consisting of amino acid sequence expressed by SEQ ID NO:3 of inter-alpha-trypsin inhibitor heavy chain H4 precursor wherein healthy controls are shown as NR.

FIG. 3 shows the results of the immunoMS assay for 2 healthy controls (NR), 5 fatty liver patients (FL) and 13

NASH patients (NS). The mean and standard deviation (bar) are shown for duplicate or triplicate determinations of each sample. IDs that are identical to those in Example 2 are indicated for FL and NS but those for CH do not correspond to each other. The threshold value of 8.3 fmol/μL for serum concentration of the glycated peptide is indicated by the stippled line. The number of cases exceeding the threshold/total number of cases was found to be 0/2 for healthy controls, 1/5 for fatty liver patients and 11/13 for NASH patients. Obviously, the values were high in NASH patients. The mean and standard deviation of serum concentration (fmol/μL) were as follows (number of subjects in parenthesis): healthy controls, 1.75, 2.47 (2); fatty liver patients, 6.36, 5.18 (5); NASH patients, 17.10, 9.11 (13); chronic hepatitis patients, 17.93, 13.82 (2).

Figure 4:
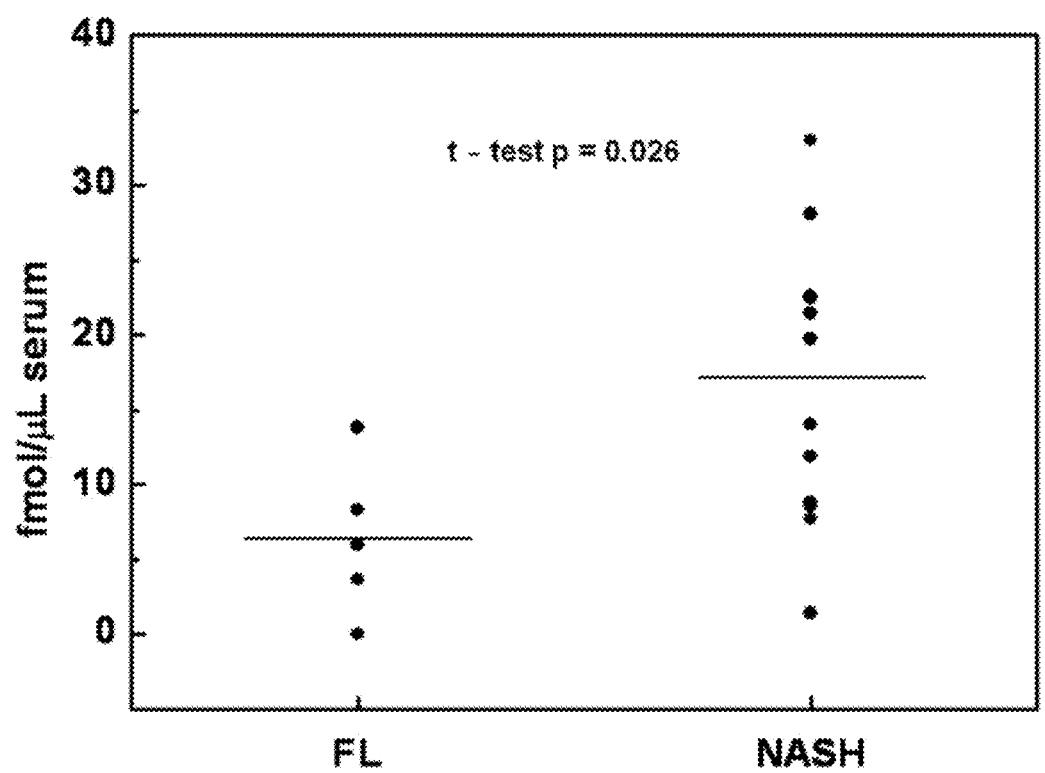
FIG. 4 illustrates the scatter plots for serum concentrations as determined by immunoMS method of glycated partial peptide consisting of amino acid sequence expressed by SEQ ID NO:3 of inter-alpha-trypsin inhibitor heavy chain H4 precursor wherein fatty liver (FL) and NASH are compared.

FIG. 4 is a scatter diagram of the results for fatty liver and NASH shown in FIG. 3. The respective mean values are 6.36 fmol/μL and 17.10 fmol/μL as described above. The p value from t-test being 0.026 indicates that patients with NASH are significantly higher in serum concentration of glycated partial peptide (SEQ ID NO:3) of inter-alpha-trypsin inhibitor heavy chain H4 precursor than those with fatty liver.

Figure 5:
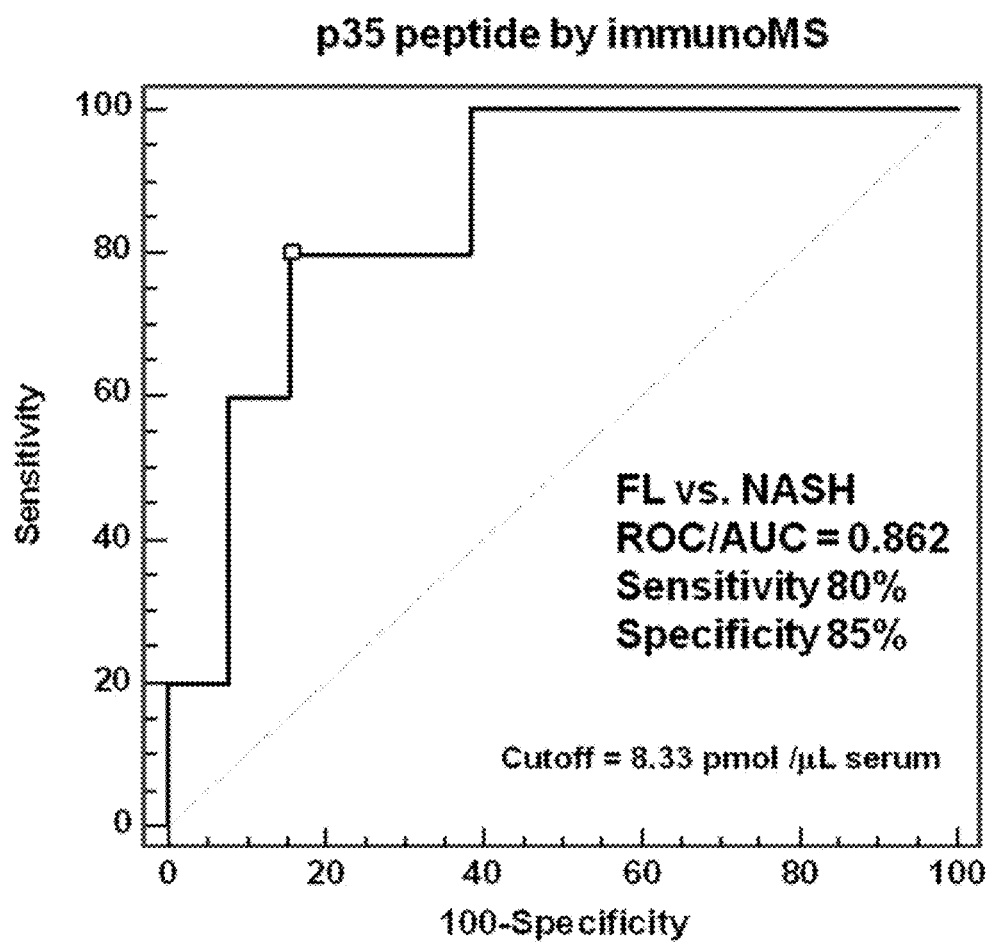
FIG. 5 shows the ROC curve and the value for AUC of serum concentrations determined by immunoMS method of glycated partial peptide consisting of amino acid sequence expressed by SEQ ID NO:3 of inter-alpha-trypsin inhibitor heavy chain H4 precursor and demonstrates that said partial peptide is capable of differentially diagnose between fatty liver (FL) and NASH.

FIG. 5 shows the ability of differential diagnosis between fatty liver and NASH in terms of the Receiver Operating Characteristics (ROC) Curve and the corresponding Area under the Curve (AUC). The AUC is 0.862, indicating that the glycated partial peptide of inter-alpha-trypsin inhibitor heavy chain H4 precursor is a useful diagnostic marker differentiating between fatty liver and NASH. Note that, in FIG. 5, the glycated partial peptide (SEQ ID NO:3) of inter-alpha-trypsin inhibitor heavy chain H4 precursor is expressed as p35 peptide.

Example 5

Construction of ELISA for determination of the 35 kDa protein fragment of inter-alpha-trypsin inhibitor heavy chain H4 precursor A sandwich method where the antigen is sandwiched with two antibodies having different epitopes attaching to both ends of it is constructed. The antibodies can be either polyclonal or monoclonal. Described herein is the case for polyclonal antibodies.

The antibody, BMPEP1117R, was shown in Example 3 (FIG. 2) to react with the N-terminus of the 35 kDa protein fragment (SEQ ID NO:2) of inter-alpha-trypsin inhibitor heavy chain H4 precursor. To confirm further that BMPEP1117R captures this fragment and that the fragment thus captured reacts with an antibody specific to the C-terminus of the 35 kDa protein fragment (SEQ ID NO:2), the following experiments were carried out.

An antibody specific to the C-terminus (herein called BMPEP1117C) was prepared, according to the method described in Example 1, by using partial peptide SATRERRLDYQEGPPGVEIS (SEQ ID NO: 9) (217-236) of SEQ ID NO:2 as the immunogen. The antibody was obtained as the IgG fraction from antiserum. The antibody was cross-linked to Protein G Sepharose using dimethyl pimelimidate (DMP) to yield "antibody beads." Experiments to see whether BMPEP1117R captures the 35 kDa protein fragment were done by using these antibody beads, which were stored in the form of suspension prepared by adding 2 volumes of TBS to one volume of wet beads.

Thirty-five microliter each of serum samples from 3 patients with chronic hepatitis, in which the presence of the 35 kDa protein fragment of inter-alpha-trypsin inhibitor heavy chain H4 precursor had been confirmed, was mixed with 1 mL TBS and the stored antibody beads suspension (30 μL) was added. The resulting mixture was slowly stirred at room temperature for 2 h and transferred to a spin column. The antibody beads were washed several times with TBS by centrifugation and, finally, the protein fragment captured by the antibody beads was eluted with 100 μL 0.2 M glycine-HCl (pH 2.5) twice. A total of 200 μL supernatant obtained was neutralized with 1 M Tris and concentrated to a volume of 40 μL using microcon 10 (MILLIPORE) by repeated centrifugation during which the solvent was exchanged to 20 mM phosphate buffer (pH 7.0). The resulting concentrate was subjected to SDS-PAGE with 10% acryl amide gel and Western blotting was carried out by using BMPEP1117C (1:1000) as the primary antibody and HRP conjugated anti-rabbit IgG (1:5000) (GE Healthcare) as the secondary antibody.

Figure 6:
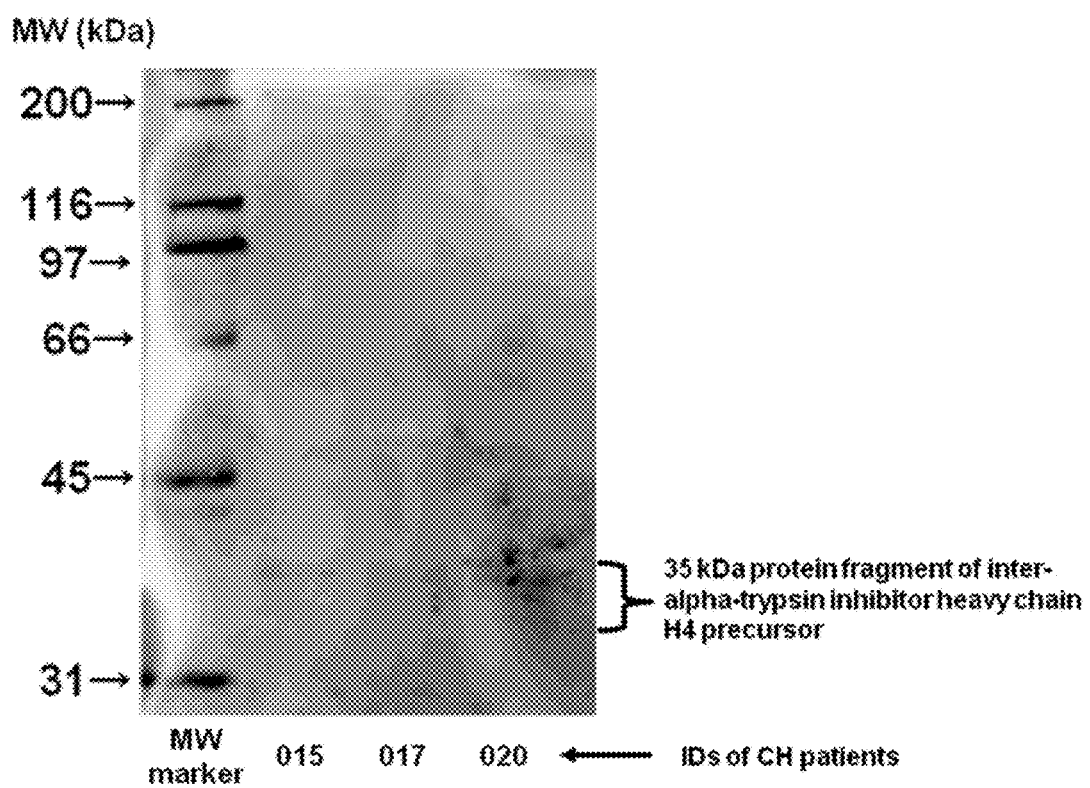
FIG. 6 illustrates the fact that BMPEP1117R actually captured the 35 kDa protein fragment of inter-alpha-trypsin inhibitor heavy chain H4 precursor and that the captured fragment reacted with antibody specific to its C-terminus (BMPEP1117C).

FIG. 6 shows the results of Western blotting described above. In all of the samples from the 3 patients with chronic hepatitis tested, several bands were observed in the neighborhood of 35 kDa and their locations coincided with those in FIG. 2. These results demonstrate that BMPEP1117R captures the 35 kDa protein fragment (SEQ ID NO:2) of inter-alpha-trypsin inhibitor heavy chain H4 precursor and that the fragment thus captured reacts with the antibody specific to its C-terminus. It is therefore shown that the construction of ELISA for measurement of the 35 kDa protein fragment (SEQ ID NO:2) of inter-alpha-trypsin inhibitor heavy chain H4 precursor is enabled.

INDUSTRIAL APPLICABILITY

As nonalcoholic fatty liver disease including nonalcoholic steatohepatitis can be detected by using the biomarkers disclosed in the present invention, the invention is applicable to the use in the field of medical diagnosis including that of diagnostic agents.

The invention claimed is:

1. A method of diagnosing and treating nonalcoholic steatohepatitis in a human patient comprising:
   a. generating a rabbit polyclonal antibody by immunizing rabbits with an immunogen, wherein the immunogen consists of SEQ ID NO: 7 conjugated to keyhole limpet hemocyanin (KLH);
   b. obtaining a sample from a human patient, wherein said sample is blood or serum;
   c. contacting the sample with the rabbit polyclonal antibody generated at step a.;
   d. detecting binding between the rabbit polyclonal antibody and at least one biomarker in said sample, wherein the at least one biomarker is selected from the group consisting of:
      (i) the protein consisting of SEQ ID NO: 2,
      (ii) the peptide consisting of SEQ ID NO: 3, and
      (iii) a glycosylated peptide consisting of SEQ ID NO: 3, wherein the glycosylated peptide comprises SEQ ID NO: 3 bound to -GlcNAc-Hex-GlcNAc-Hex;
   e. diagnosing the patient as having nonalcoholic steatohepatitis when the at least one biomarker is detected in higher quantity than in a healthy control subject, wherein the healthy control subject does not have nonalcoholic steatohepatitis; and
   f. administering treatment to the patient when the patient is diagnosed with nonalcoholic steatohepatitis, wherein said treatment is selected from the group consisting of diet and drug therapy.

2. A method of diagnosing and treating nonalcoholic steatohepatitis in a human patient comprising:
   a. generating a rabbit polyclonal antibody by immunizing rabbits with an immunogen comprising an amino acid sequence, wherein the sequence consists of SEQ ID NO: 9;
   b. obtaining a sample from a human patient, wherein said sample is blood or serum;
   c. contacting the sample with the rabbit polyclonal antibody generated at step a.;
   d. detecting binding between the rabbit polyclonal antibody and at least one biomarker in said sample, wherein the at least one biomarker is selected from the group consisting of:
      (i) the protein consisting of SEQ ID NO: 1, and
      (ii) the protein consisting of SEQ ID NO: 2;
   e. diagnosing the patient as having nonalcoholic steatohepatitis when the at least one biomarker is detected in higher quantity than in a healthy control subject, wherein the healthy control subject does not have nonalcoholic steatohepatitis; and
   f. administering treatment to the patient when the patient is diagnosed with nonalcoholic steatohepatitis, wherein said treatment is selected from the group consisting of diet and drug therapy.

3. A method of diagnosing nonalcoholic steatohepatitis in a human patient comprising:
   a. generating a rabbit polyclonal antibody by immunizing rabbits with an immunogen consisting of SEQ ID NO: 7 conjugated to KLH;
   b. obtaining a sample from a human patient, wherein said sample is blood or serum;
   c. contacting the sample with the rabbit polyclonal antibody generated at step a.;
   d. detecting binding between the rabbit polyclonal antibody and at least one biomarker in said sample, wherein the at least one biomarker is selected from the group consisting of:
      (i) the protein consisting of SEQ ID NO: 2,
      (ii) the peptide consisting of SEQ ID NO: 3, and
      (iii) a glycosylated peptide consisting of SEQ ID NO: 3, wherein the glycosylated peptide comprises SEQ ID NO: 3 bound to -GlcNAc-Hex-GlcNAc-Hex;
   e. diagnosing the patient with nonalcoholic steatohepatitis when the at least one biomarker is detected in higher quantity than in a healthy control subject,
   wherein the healthy control subject does not have nonalcoholic steatohepatitis.

4. A method of diagnosing nonalcoholic steatohepatitis in a human patient comprising:
   a. generating a rabbit polyclonal antibody by immunizing rabbits with an immunogen comprising a sequence, wherein the sequence consists of SEQ ID NO: 9;
   b. obtaining a sample from a human patient, wherein the sample is blood or serum;
   c. contacting the sample with the rabbit polyclonal antibody generated at step a.;
   d. detecting binding between the rabbit polyclonal antibody and at least one biomarker in said sample, wherein the at least one biomarker is selected from the group consisting of:
      (i) the protein consisting of SEQ ID NO: 1, and
      (ii) the protein consisting of SEQ ID NO: 2,
   e. diagnosing the patient as having nonalcoholic steatohepatitis when the at least one biomarker is detected in higher quantity than in a healthy control subject,
   wherein the healthy control subject does not have nonalcoholic steatohepatitis.

* * * * *

SEQUENCE LISTING

```
<160> NUMBER OF SEQ ID NOS: 9

<210> SEQ ID NO 1
<211> LENGTH: 930
<212> TYPE: PRT
<213> ORGANISM: Homo sapiens

<400> SEQUENCE: 1

Met Lys Pro Pro Arg Pro Val Arg Thr Cys Ser Lys Val Leu Val Leu
1               5                   10                  15

Leu Ser Leu Leu Ala Ile His Gln Thr Thr Ala Glu Lys Asn Gly
            20                  25                  30

Ile Asp Ile Tyr Ser Leu Thr Val Asp Ser Arg Val Ser Ser Arg Phe
        35                  40                  45
```

```
Ala His Thr Val Val Thr Ser Arg Val Val Asn Arg Ala Asn Thr Val
    50                  55                  60
Gln Glu Ala Thr Phe Gln Met Glu Leu Pro Lys Lys Ala Phe Ile Thr
65                  70                  75                  80
Asn Phe Ser Met Asn Ile Asp Gly Met Thr Tyr Pro Gly Ile Ile Lys
                85                  90                  95
Glu Lys Ala Glu Ala Gln Ala Gln Tyr Ser Ala Ala Val Ala Lys Gly
            100                 105                 110
Lys Ser Ala Gly Leu Val Lys Ala Thr Gly Arg Asn Met Glu Gln Phe
        115                 120                 125
Gln Val Ser Val Ser Val Ala Pro Asn Ala Lys Ile Thr Phe Glu Leu
    130                 135                 140
Val Tyr Glu Glu Leu Leu Lys Arg Arg Leu Gly Val Tyr Glu Leu Leu
145                 150                 155                 160
Leu Lys Val Arg Pro Gln Gln Leu Val Lys His Leu Gln Met Asp Ile
                165                 170                 175
His Ile Phe Glu Pro Gln Gly Ile Ser Phe Leu Glu Thr Glu Ser Thr
            180                 185                 190
Phe Met Thr Asn Gln Leu Val Asp Ala Leu Thr Thr Trp Gln Asn Lys
        195                 200                 205
Thr Lys Ala His Ile Arg Phe Lys Pro Thr Leu Ser Gln Gln Gln Lys
    210                 215                 220
Ser Pro Glu Gln Gln Glu Thr Val Leu Asp Gly Asn Leu Ile Ile Arg
225                 230                 235                 240
Tyr Asp Val Asp Arg Ala Ile Ser Gly Gly Ser Ile Gln Ile Glu Asn
                245                 250                 255
Gly Tyr Phe Val His Tyr Phe Ala Pro Glu Gly Leu Thr Thr Met Pro
            260                 265                 270
Lys Asn Val Val Phe Val Ile Asp Lys Ser Gly Ser Met Ser Gly Arg
        275                 280                 285
Lys Ile Gln Gln Thr Arg Glu Ala Leu Ile Lys Ile Leu Asp Asp Leu
    290                 295                 300
Ser Pro Arg Asp Gln Phe Asn Leu Ile Val Phe Ser Thr Glu Ala Thr
305                 310                 315                 320
Gln Trp Arg Pro Ser Leu Val Pro Ala Ser Ala Glu Asn Val Asn Lys
                325                 330                 335
Ala Arg Ser Phe Ala Ala Gly Ile Gln Ala Leu Gly Gly Thr Asn Ile
            340                 345                 350
Asn Asp Ala Met Leu Met Ala Val Gln Leu Leu Asp Ser Ser Asn Gln
        355                 360                 365
Glu Glu Arg Leu Pro Glu Gly Ser Val Ser Leu Ile Ile Leu Leu Thr
    370                 375                 380
Asp Gly Asp Pro Thr Val Gly Glu Thr Asn Pro Arg Ser Ile Gln Asn
385                 390                 395                 400
Asn Val Arg Glu Ala Val Ser Gly Arg Tyr Ser Leu Phe Cys Leu Gly
                405                 410                 415
Phe Gly Phe Asp Val Ser Tyr Ala Phe Leu Glu Lys Leu Ala Leu Asp
            420                 425                 430
Asn Gly Gly Leu Ala Arg Arg Ile His Glu Asp Ser Asp Ser Ala Leu
        435                 440                 445
Gln Leu Gln Asp Phe Tyr Gln Glu Val Ala Asn Pro Leu Leu Thr Ala
    450                 455                 460
```

-continued

Val Thr Phe Glu Tyr Pro Ser Asn Ala Val Glu Val Thr Gln Asn
465                 470                 475                 480

Asn Phe Arg Leu Leu Phe Lys Gly Ser Glu Met Val Val Ala Gly Lys
            485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
            515                 520                 525

Gln Glu Ala Glu Phe Gln Ser Pro Lys Tyr Ile Phe His Asn Phe Met
530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
            595                 600                 605

Met Glu Gly Glu Ser Arg Asn Arg Asn Val His Ser Gly Ser Thr Phe
610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Leu Leu Gly Leu
            660                 665                 670

Pro Gly Pro Pro Asp Val Pro Asp His Ala Ala Tyr His Pro Phe Arg
            675                 680                 685

Arg Leu Ala Ile Leu Pro Ala Ser Ala Pro Ala Thr Ser Asn Pro
690                 695                 700

Asp Pro Ala Val Ser Arg Val Met Asn Ile Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
            755                 760                 765

Val Thr Gly Gln Tyr Glu Arg Glu Lys Ala Gly Phe Ser Trp Ile Glu
            770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
            835                 840                 845

Phe Trp Asp Gly Arg Gly Glu Gly Leu Arg Leu Leu Leu Arg Asp Thr
            850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr

```
                    885                 890                 895
Leu Arg Val Gln Gly Asn Asp His Ser Ala Thr Arg Glu Arg Leu
                900                 905                 910

Asp Tyr Gln Glu Gly Pro Pro Gly Val Glu Ile Ser Cys Trp Ser Val
                915                 920                 925

Glu Leu
    930

<210> SEQ ID NO 2
<211> LENGTH: 242
<212> TYPE: PRT
<213> ORGANISM: Homo sapiens

<400> SEQUENCE: 2

Arg Leu Ala Ile Leu Pro Ala Ser Ala Pro Ala Thr Ser Asn Pro
1               5                  10                  15

Asp Pro Ala Val Ser Arg Val Met Asn Ile Lys Ile Glu Glu Thr Thr
                20                  25                  30

Met Thr Thr Gln Thr Pro Ala Pro Ile Gln Ala Pro Ser Ala Ile Leu
            35                  40                  45

Pro Leu Pro Gly Gln Ser Val Glu Arg Leu Cys Val Asp Pro Arg His
50                  55                  60

Arg Gln Gly Pro Val Asn Leu Leu Ser Asp Pro Glu Gln Gly Val Glu
65                  70                  75                  80

Val Thr Gly Gln Tyr Glu Arg Glu Lys Ala Gly Phe Ser Trp Ile Glu
                85                  90                  95

Val Thr Phe Lys Asn Pro Leu Val Trp Val His Ala Ser Pro Glu His
                100                 105                 110

Val Val Val Thr Arg Asn Arg Arg Ser Ser Ala Tyr Lys Trp Lys Glu
                115                 120                 125

Thr Leu Phe Ser Val Met Pro Gly Leu Lys Met Thr Met Asp Lys Thr
    130                 135                 140

Gly Leu Leu Leu Leu Ser Asp Pro Asp Lys Val Thr Ile Gly Leu Leu
145                 150                 155                 160

Phe Trp Asp Gly Arg Gly Glu Gly Leu Arg Leu Leu Arg Asp Thr
                165                 170                 175

Asp Arg Phe Ser Ser His Val Gly Gly Thr Leu Gly Gln Phe Tyr Gln
                180                 185                 190

Glu Val Leu Trp Gly Ser Pro Ala Ala Ser Asp Asp Gly Arg Arg Thr
    195                 200                 205

Leu Arg Val Gln Gly Asn Asp His Ser Ala Thr Arg Glu Arg Leu
    210                 215                 220

Asp Tyr Gln Glu Gly Pro Pro Gly Val Glu Ile Ser Cys Trp Ser Val
225                 230                 235                 240

Glu Leu

<210> SEQ ID NO 3
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: O-linked Glycosylation
<220> FEATURE:
<221> NAME/KEY: MOD_RES
<222> LOCATION: (13)..(13)
<223> OTHER INFORMATION: O-linked Glycosylation
```

```
<220> FEATURE:
<221> NAME/KEY: MOD_RES
<222> LOCATION: (14)..(14)
<223> OTHER INFORMATION: O-linked Glycosylation

<400> SEQUENCE: 3

Arg Leu Ala Ile Leu Pro Ala Ser Ala Pro Pro Ala Thr Ser Asn Pro
1               5                   10                  15

Asp

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ile Arg Gly Glu Arg Ala
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ile Lys Gly Glu Arg Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Cys Gly Gly Gly Glu Arg Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: modified with carrier protein, KLH

<400> SEQUENCE: 7

Arg Leu Ala Ile Leu Pro Ala Ser Cys
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Arg Leu Ala Ile Leu Pro Ala Ser Ala Pro Pro Ala Thr Ser Asn Pro
```

```
                1               5              10              15
Asp

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Ser Ala Thr Arg Glu Arg Arg Leu Asp Tyr Gln Glu Gly Pro Pro Gly
1               5                  10                  15

Val Glu Ile Ser
            20
```